United States Patent [19]

Sömmer et al.

[11] Patent Number: 5,430,030
[45] Date of Patent: Jul. 4, 1995

[54] NERVE GAS ANTIDOTE

[75] Inventors: Armin Sömmer, Radebeul; Bleyer Holm, Greifswald, both of Germany

[73] Assignee: Arzneimittelwerk Dresden GmbH, Radebeul, Germany

[21] Appl. No.: 166,883

[22] Filed: Dec. 15, 1993

Related U.S. Application Data

[62] Division of Ser. No. 882,591, May 13, 1992, Pat. No. 5,298,504.

[30] Foreign Application Priority Data

May 13, 1992 [DE] Germany .................. 41 15 558.0

[51] Int. Cl.$^6$ .................. A61K 31/55; A61K 31/40; A01N 25/32
[52] U.S. Cl. .................. 514/221; 424/406; 424/408; 424/456; 424/464; 424/468; 514/411; 514/415; 514/317; 514/327; 514/520; 514/823; 514/351; 514/534
[58] Field of Search .............. 424/406, 408, 456, 464, 424/468; 514/411, 415, 221, 317, 327, 520, 823, 351, 534

[56] References Cited

FOREIGN PATENT DOCUMENTS 2821778 12/1979 Germany .

OTHER PUBLICATIONS

J. Pharm. Pharmcol., vol. 29, No. 1., 1977, pp. 62–64, CODEN:ISSN:JPPM, Green, D. M. et al., "Dual Mechanism of the Antidotal Action . . . ".
J. Pharm. Pharmcol., vol. 42, No. 4, pp. 247–251, 1990, Karlsson, B. et al., "On the Use of Diazepam and Pro . . . ".
Toxicology, vol. 27, No. 1, pp. 41–54, 1983, Klemm, W. R. "Efficacy and Toxicity of Drug Combinations . . . ".
Chemical Abstracts, vol. 104, No. 13, Mar. 31, 1986, No. 103801, Leadbeater, L. et al., "Treatment of Poisoning by Soman".
Fundam. Appl. Toxicol., vol. 5, No. 6, Pt. 2, pp. S225–S231, 1985, Leadbeater, L., "Treatment of Poisoning by Soman".
Chemical Abstracts, vol. 92, p. 156, No. 16490v, 1980, Davoson, R. M., "Some Adjuncts to Oxime-Atropine . . . ".
Chemical Abstracts, vol. 85, p. 123, No. 57639z, 1976, O'Leary, J. F., "A Comparative Evaluation of Atropine . . . ".
SB VED LEK FAK KARLOVY UNIVERZITY HRADCI KRALOVE, 1991, vol. 34, No. 3, pp. 243–247, Patocka, J. et al., "Efficacy of Various Pretreatment and Therapy Regimens Against Soman Lethality in Mice".
Pharmacol. Toxicol., vol. 67, No. 1, pp. 27–35, 1990, Bataillard, A. et al. "Cardiovascular Consequences of Organo-. . . ".

Primary Examiner—Marianne M. Cintins
Assistant Examiner—T. J. Criares
Attorney, Agent, or Firm—Cushman Darby & Cushman

[57] ABSTRACT

A prophylactic pretreatment for nerve gas and pesticide poisons which can be administered orally and which comprises the following agents, in combination: a. Pyridostigmine (pyridostigmine bromide) b. Diazepam c. N-methyl-4-pipyridinyl phenylcyclopentanecarboxylate These agents may be administered in the form of a capsule which contains, for example, tablets, one a normal release dosage form and one or two in a slow release dosage form.

5 Claims, No Drawings

NERVE GAS ANTIDOTE

This is a division of application Ser. No. 07/882,591, filed May 13, 1992, now U.S. Pat. No. 5,298,504.

The present invention relates to an oral prophylactic useful for minimizing injury from nerve gas poisons and related compounds such as organophosphorus pesticides.

BACKGROUND OF THE INVENTION

Nerve gas poisons are organic esters of substituted phosphoric acids. They inhibit cholinesterase enzymes and therefore are classified as anticholinesterase agents. Three active agents include Tabun (ethyl phosphorodimethylamidocyanidate -$((CH_3)_2NP(O)(CN)OC_2H_5$ GA), Sarin (isopropyl methylphosphonofluoridate - $CH_3P(O)(F)OCH(CH_3)_2$-GB) and Soman (pinocolyl methylphosphonofluoridate -$CH_3P(O)(F)OCH(CH_3)C(CH_3)_3$-GD). These compounds are highly volatile and easily disseminated in vapor form. They are readily absorbed through the lungs and eyes, and also the skin and intestinal tract without producing any irritation or other sensation. They are sufficiently potent that even brief exposure may be fatal. Depending on the concentration of the poison, death may occur in as little as one minute, or it may be delayed for 1–2 hours.

Another category of such agents is the V agents, which are more potent, including VX.

Chemically related insecticides include parathion, methyl parathion and malathion, and these exhibit similar toxicity, although they are generally less potent.

Known treatments for these agents include medications which are administered after exposure to the poisons, such as atropine. Prophylactic agents have been investigated, but, in spite of intensive research, only a small number of agents have been identified which offer effective and safe protection against these agents.

Published German Patent Application DE 28 21 778 discloses a prophylactic antidote for organophosphorus pesticides which protects agricultural workers against lethal pesticides during the course of one workday. The agent administered includes hyoscine butyl bromate, a propanol chlorhydrate, dimethyl-carbamoxy-phenyl-trimethyl ammonium bromate and ephedrine. Leadbeater et al, Fundamental and Applied Toxicology Vol. 5, pages S225-S231 (1985) disclose a prophylactic pretreatment comprising an injection with a carbamate and anti-cholinergic drugs such as Aprophene (2-diethylaminoethyl-α-α-diphenylpropionate), Hyoscine, Adiphenine, Caramiphen, Dicyclomine and G 3063 (N-methyl-4-pipyridinyl phenylcyclopentanecarboxylate). Carbamates which are mentioned included pyridostigmine and physostigmine. The authors also demonstrated the combined effect of pretreatment with pyridostigmine or physostigmine, with and without Atrophen and post-treatment with a variety of other medications (atropine, P2S and diazepam).

There is a need for more effective prophylactic pretreatments for the foregoing toxic agents. It is desirable to protect against twice the toxic dose, since this is thought to be the maximum possible field concentration. It is desirable that the treatment be administered orally, rather than by injection, that it provide protection for a long time, 10–12 hours, and that treatment can be repeated during an extended period of time, for example 5 days (10 doses) without severely diminishing the patients ability to function or fight in a combat environment.

SUMMARY OF THE INVENTION

The present invention provides a prophylactic pretreatment which can be administered orally and which comprises the following agents, in combination:

a. Pyridostigmine (pyridostigmine bromide) or physostigmine b. Diazepam or clonazepam c. G 3063, Arpenal, Sycotrol (pipetabanate hydrochloride), caramiphen (caramiphene hydrochloride) or benactyzine (benactyzine hydrochloride).

These agents are administered in the form of a capsule which contains, for example, tablets, one a normal release dosage form and one or two in a slow release dosage form. Based on the biological half life of the substances in humans and the desired duration of protection, the components are distributed between the normal release component and the slow release component in the following total amounts:

a. 30–60 mg pyridostigmine or 0.5–2.0 mg physostigmine b. 3–5 mg diazepam or 0.5–2.0 mg clonazepan c. 3–8 mg G3063, 5.0–15 mg arpenal, 2–10 mg sycotrol, 5.0–15 mg caramiphen or 3–20 mg benactyzine.

The formulas of these compounds are shown below:

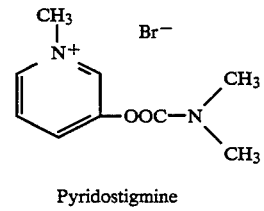

Pyridostigmine

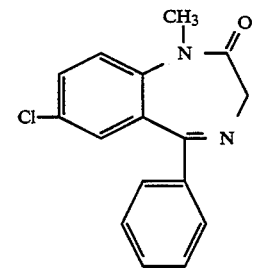

Diazepam

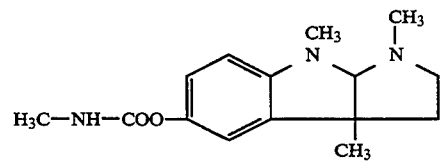

Physostigmine

-continued

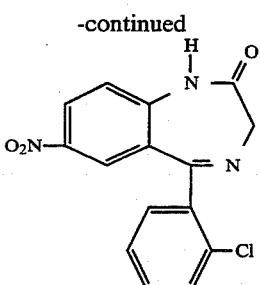

Clonazepam

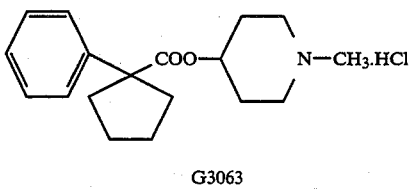

G3063

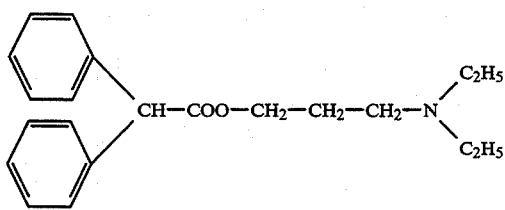

Arpenal

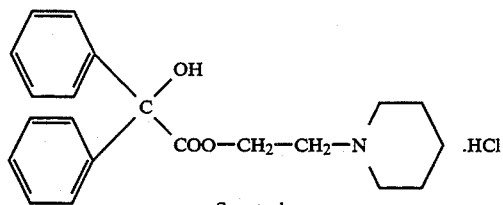

Sycotrol

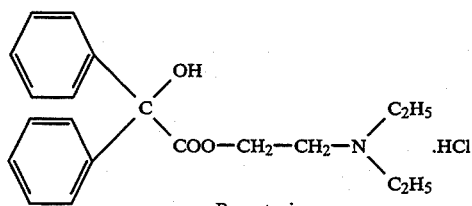

Benactyzine

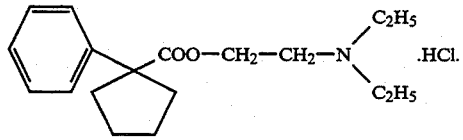

Caramiphene

It is not necessary that all of the components be included in both the slow release component and the normal release component. For example, in a preferred composition, the normal release component contains 20 mg pyridostigmine (component a) and 3 mg diazepam (component b) and the delayed release component contains 30 mg. pyridostigmine (component a) and 5 mg G 3063 (component c). A second preferred composition includes a normal release component consisting of 20 mg pyridostigmine (component a) and 3 mg diazepam (component b) and the delayed release component contains 30 mg pyridostigmine (component a) and 10 mg Arpenal (Component C).

In all preferred compositions, it is possible to substitute 1.5 mg of physostigmine for a total of 50 mg of pyridostigmine, distributed between the two components. This can be expected to provide stronger protection, as is seen in Table 8, but also a considerable loss of the ability of the person treated to function. Comparable results are obtained by replacing diazepam with 1.0 mg. clonazepam. Substitution of alternatives for G 3063 reduces both the level of protection and, to some extent, the functioning ability of the person treated. Among the alternatives for component c, the preferred order of use is G 3063, Arpenal, Sycotrol, caramiphen and benactyzine. In place of 5.0 mg. G3063 or 10.0 mg. arnepal, it is possible to use 5.0 mg. sycotrol, 8.0 rag. caramaphene, or 10 mg. benactyzine. Approximately equivalent values are desirable for the blood level and protection time.

The pyridostigmine and physostigmine doses (human) are selected with a view to lowering serum cholinesterase activity to 70-80% of the initial value over a period of 10-12 hours. This long term effect is achieved by distributing the dose between the normal release component and the delayed release component. Similar values for blood levels and duration of protection determine the doses and distribution of the other agents.

To separate the active components into the two components, the immediate release component and the delayed release component, for use in humans, two factors must be considered:

1. The goal of a prophylactic effect of 10 to 12 hours.
2. The biological half-life of the components in humans.

The length of the effect of diazepam and clonazepam is known. They do not required a delayed release effect.

The short length of effectiveness of the components of group c must be compensated by delayed release to obtain the first above-mentioned goal. This assures the effectiveness of the medicine from the time of administration throughout the desired period of effectiveness.

In the case of component a, the desired 70-80% of the initial cholinesterase activity can be achieved with a normal release medicinal form. The desired length of effectiveness can be extended by including part of component c in the delayed release component.

It is uneconomical to try to achieve delivery of the medication over a longer period than about 12 hours.

In the preferred form of the invention, the normal release component is formed into a single tablet, and the delayed release component is formed into one or two tablets. The tablets are then enclosed in a gelatin capsule.

The invention provides the following advantages compared to previously known treatments:

The composition can be administered orally. Thus, the composition can be self-administered, without assistance of medical personnel. Effective protection can be provided over a prolonged period with only a single dose taken every 12 hours, without danger of accumulation in the patient. Any combination from each of the three groups, a, b and c produces a novel level of protection against the poisonous effects of highly toxic organophosphorus agents. The preferred qualitative and quantitative combinations offer a high level of protection without diminished functioning capabilities.

A therapeutic agent can also be administered after exposure to the poisons. In such cases, the therapeutic index can be greatly increased.

The efficacy of the composition was determined in animals against exposure to Soman, Sarin and VX. In these experiments, the degree of efficacy was expressed as the prophylactic index, equal to the quotient:

$$\frac{LD_{50} \text{ with antidote}}{LD_{50} \text{ without antidote}} = \text{prophylactic index of the antidote}$$

The performance of the prophylactic effect of the individual substance combinations in animal experiments are shown in the following tables:

Tables 1–3 show the prophylactic index in rats of the substance combinations supplying (a) 8 mg/kg pyridostigmine, (b) 10 mg/kg diazepam and (c) 10 mg/kg G 3063, 50 mg/kg Arpenal, 13.3 mg/kg Sycotrol or 5.25 mg/kg caramiphen. Tables 4–7 demonstrate that a still higher therapeutic index can be achieved in rats if a therapeutic antidote (TOA) is given after exposure with the toxic agent. The results are reported with the prophylactic agents of Tables 1 and 2, and administration of the therapeutic antidote (TOA) either 3 or 6 minitues after exposure to the toxic agent.

Table 8 demonstrates the therapeutic index of the antidote combination 1.2 mg/kg physostigmine, 10 mg/kg diazepam an 10 mg/kg G 3063 in rats.

Table 9 provides data on survival rates in rabbits in relationship to the time between the prophylactic administration of 6.0 mg/kg pyridostigmine, 10.0 mg/kg diazepam and 10 mg/kg G203063 and the time of acute intoxication with Soman.

TABLE 1

The effect of the combination of 8 mg/kg pyridosdgmine, 10 mg/kg diazepam, 10 mg/kg G 3063 on the acute toxicity of Soman, Sarin and VX In relationship to the time of prophylaxis (rats)
Potentation Rate of the $LD_{50}$

| Poison | Prophylaxis (min) | | | | |
|---|---|---|---|---|---|
| | 30 | 60 | 120 | 180 | 300 |
| Soman | 2.55 | 2.35 | 2.03 | 1.87 | 1.87 |
| Sarin | 2.28 | 5.00 | 2.88 | 2.50 | 1.48 |
| VX | 13.75 | 12.67 | 9.75 | 6.42 | 1.83 |

TABLE 2

The effect of the combination 8 mg/kg pyridostigmine, 10 mg/kg diazepam and 40 mg/kg Arsenal on the acute toxicity of Soman, Sarin and VX in relationship to the time of prophylaxis (rats)
Potentation Rate of the $LD_{50}$

| Poison | Prophylaxis (min) | | | | |
|---|---|---|---|---|---|
| | 30 | 60 | 120 | 180 | 300 |
| Soman | 2.77 | 2.20 | 1.37 | 1.06 | 1.33 |
| Sarin | 2.01 | 2.54 | 1.41 | 1.27 | 1.12 |
| VX | 2.80 | 2.53 | 2.33 | 1.73 | 1.80 |

TABLE 3

The effect of the prophylactic administration (30 minutes prior to exposure to the poison) of two combinations (a) 8 mg/kg pyridostigmine, 10 mg/kg diazepam and 13.3 mg/kg Sycotrol and (b) 8 mg/kg pyridosdgmine, 10 mg/kg diazepam and 5.25 mg/kg caramiphen on the acute toxicity of Soman, Sarin and VX (rats)
Potentation Rate of the $LD_{50}$

| Poison | with caramiphen | with Sycotrol |
|---|---|---|
| Soman | 1.47 | 1.26 |
| Sarin | 2.00 | 2.03 |

TABLE 3-continued

The effect of the prophylactic administration (30 minutes prior to exposure to the poison) of two combinations (a) 8 mg/kg pyridostigmine, 10 mg/kg diazepam and 13.3 mg/kg Sycotrol and (b) 8 mg/kg pyridosdgmine, 10 mg/kg diazepam and 5.25 mg/kg caramiphen on the acute toxicity of Soman, Sarin and VX (rats)
Potentation Rate of the $LD_{50}$

| Poison | with caramiphen | with Sycotrol |
|---|---|---|
| VX | 1.44 | 1.92 |

TABLE 4

The effect of the prophylactic administration of the combination 8 mg/kg pyridostigmine, 10 mg/kg diazepam and 10 mg/kg G 3063 and administration of TOA three minutes after exposure to the poison on the acute toxicity of Soman, Sarin and VX (rate)
Potentiation Rate of the $LD_{50}$

| Poison | Prophylaxis (min) | | | | |
|---|---|---|---|---|---|
| | 30 | 60 | 120 | 180 | 300 |
| Soman | 2.55 | 2.50 | 2.88 | 2.88 | 2.35 |
| Sarin | 6.92 | 7.06 | 4.62 | 5.60 | 3.08 |
| VX | 38.88 | 33.36 | 29.85 | 29.85 | 14.93 |

TABLE 5

The effect of the prophylactic administration of the combination of 8 mg/kg pyridostigmine, 10 mg/kg diazepam and 10 mg/kg G 3063 and administration of TOA six minutes after exposure to the poison, on the acute toxicity of Soman, Sarin and VX (rats)
Potentiation Rate of the $LD_{50}$

| Poison | Prophylaxis (min) | | | | |
|---|---|---|---|---|---|
| | 30 | 60 | 120 | 180 | 300 |
| Soman | 2.42 | 2.42 | 2.21 | 2.41 | 2.62 |
| Sarin | 5.95 | 5.86 | 6.93 | 3.62 | 2.54 |
| VX | 38.46 | 42.10 | 23.10 | 7.69 | 7.69 |

TABLE 6

The effect of the prophylactic administration of the combination 8 mg/kg pyridostigmine, 10 mg/kg diazepam, 40 mg/kg Arsenal and administration of TOA three minutes after exposure to the poison on the acute toxicity of Soman, Sarin and VX (rats)
Potentiation Rate of the $LD_{50}$

| Poison | Prophylaxis (min) | | | | |
|---|---|---|---|---|---|
| | 30 | 60 | 120 | 180 | 300 |
| Soman | 2.40 | 2.50 | 2.70 | 2.80 | 2.10 |
| Sarin | 3.40 | 2.60 | 2.00 | 3.10 | 1.90 |
| VX | 17.50 | 15.50 | 13.30 | 12.50 | 16.30 |

TABLE 7

The effect of the prophylactic administration of the combination of 8 mg/kg pyridostigmine, 10 mg/kg diazepam and 40 mg/kg Arsenal and adminstration of TOA six minutes after exposure to the poison on the acute toxicity of Soman, Sarin and VX (rats)
Potentiation Rate of the $LD_{50}$

| Poison | Prophylaxis (min) | | | | |
|---|---|---|---|---|---|
| | 30 | 60 | 120 | 180 | 300 |
| Soman | 2.30 | 2.40 | 2.50 | 2.30 | 2.20 |
| Sarin | 3.70 | 2.20 | 2.70 | 2.80 | 2.40 |
| VX | 7.10 | 5.10 | 4.20 | 6.20 | 3.10 |

TABLE 8

The effect of the prophylactic administration (30 minutes prior to exposure to the poison) of the combination of 1.2 mg/kg phytostigmine, 10 mg/kg diazepam and 10 mg/kg G 3063 on the acute toxicity of Soman, Sarin and VX (rats)
Prophylactic Index:

| | |
|---|---|
| Soman | 3.45 |
| Sarin | 6.22 |
| VX | 18.75 |

TABLE 9

Survival rates of rabbits after acute intoxication with Soman (three times the $LD_{50}$) in relationship to prophylaxis (n = 6) with 6 mg/kg pyridostigmine, 10 mg/kg diazepam and 10 mg/kg G 3063 (POA)

| Prophylaxis (min. prior to Soman) | Survival (%) | Onset of Cramps (min.) | Occurrence of Death (min.) |
|---|---|---|---|
| 30 Min. NaCl | 0.0 | 6.05 ± 2.05 | 13.35 ± 5.25 |
| 30 Min. POA | 50 | 15.15 ± 4.35 | 110.8 ± 51 |
| 60 Min. POA | 33 | 6.40 ± 1.45 | 217.50 ± 183 |
| 120 Min. POA | 100 | 7.20 ± 3.05 | — |
| 300 Min. POA | 100 | 3.68 ± 2.19 | — |

DETAILED DESCRIPTION OF PREFERRED EMBODIMENTS

The invention is illustrated in more detail in the following examples. The dosages cited are for human administration.

EXAMPLE 1

20 mg pyridostigmine and 3 mg diazepam are processed in known manner, either separately or together, into a dosage form with normal release action. 30 mg. pyridostigmine and 5 mg G203063 are processed in known manner, either separately or together, into a dosage unit with slow release action. The two components are then combined into a single dosage unit.

EXAMPLE 2

Example 1 is repeated except that 5 mg G 3063 is replaced with 10 mg Arpenal.

EXAMPLE 3

Example 1 is repeated except that 5 mg G 3063 is replaced with 5 mg Sycotrol.

EXAMPLE 4

Example 1 is repeated except that 5 mg G 3063 is replaced with 8 mg caramiphen.

EXAMPLE 5

Example 1 is repeated except that 5 mg G 3063 is replaced with 10 mg benactyzine.

EXAMPLES 6–10

Examples 1–5 are repeated except that, in each case, 3 mg diazepam is replaced with 1.0 mg clonazepam.

EXAMPLES 11–20

Examples 1–10 are repeated except that 50 mg pyridostigmine is replaced by 1.5 mg physostigmine, distributed as 0.5 mg physostigmine in the normal release component and 1.0 mg physostigmine in the delayed release component.

What is claimed is:

1. A prophylactic antidote for phosphorganic toxins, wherein the active components of said prophylactic antidote comprise 30–60 mg pyridostigmine bromide, 3–5 mg diazepam and 3–8 mg N-methyl-4-pipyridinyl phenylcyclopentanecarboxylate.

2. The prophylactic antidote as set forth in claim 1, wherein the active components of said prophylactic antidote comprise 50 mg pyridostigmine bromide, 3 mg diazepam and 5 mg N-methyl-4-pipyridinyl phenylcyclopentanecarboxylate.

3. The prophylactic antidote as set forth in either claim 1 or 2 wherein said active components are combined in a single dosage unit form comprising a normal release solid dosage form and a delayed release solid dosage form.

4. The prophylactic antidote as set forth in claim 3 wherein each of said normal release solid dosage form and said delayed release solid dosage form is in tablet form.

5. The prophylactic antidote as set forth in claim 3, wherein said single dosage unit is in capsule form.

* * * * *

UNITED STATES PATENT AND TRADEMARK OFFICE
CERTIFICATE OF CORRECTION

PATENT NO.    : 5,430,030

DATED         : Jul. 4, 1995

INVENTOR(S)   : Armin Sömmer
                Holm Bleyer

It is certified that error appears in the above-identified patent and that said Letters Patent is hereby corrected as shown below:

Title page, items [75] and [30];

Change the second name of the inventor to
    --Holm Bleyer, Greifswald,--

Change the date listed under Foreign
    Application Priority Data to --May 13, 1991--

Signed and Sealed this

Tenth Day of October, 1995

*Attest:*

BRUCE LEHMAN

*Attesting Officer*  *Commissioner of Patents and Trademarks*